United States Patent
Hwang

(10) Patent No.: US 10,383,639 B2
(45) Date of Patent: Aug. 20, 2019

(54) DETACHABLE MEDICAL CUTTING TOOL

(71) Applicant: Jug Hee Hwang, Gyeonggi-do (KR)

(72) Inventor: Jug Hee Hwang, Gyeonggi-do (KR)

(*) Notice: Subject to any disclaimer, the term of this patent is extended or adjusted under 35 U.S.C. 154(b) by 224 days.

(21) Appl. No.: 15/220,538

(22) Filed: Jul. 27, 2016

(65) Prior Publication Data
US 2017/0265874 A1 Sep. 21, 2017

(30) Foreign Application Priority Data

Mar. 21, 2016 (KR) .................. 10-2016-0033403
Mar. 21, 2016 (KR) .................. 10-2016-0033421

(51) Int. Cl.
*A61B 17/16* (2006.01)
*A61B 17/00* (2006.01)

(52) U.S. Cl.
CPC ........ *A61B 17/1617* (2013.01); *A61B 17/162* (2013.01); *A61B 2017/0088* (2013.01); *A61B 2017/00477* (2013.01); *A61B 2017/00836* (2013.01)

(58) Field of Classification Search
CPC .................. A61B 17/1617; A61B 2017/0088
See application file for complete search history.

(56) References Cited

U.S. PATENT DOCUMENTS

| | | | | |
|---|---|---|---|---|
| 4,083,415 A | * | 4/1978 | Kita | E21B 10/38 173/132 |
| 4,190,125 A | * | 2/1980 | Emmerich | E21B 10/38 175/320 |
| 4,368,789 A | * | 1/1983 | Orr | E21B 10/38 175/418 |
| 4,615,402 A | * | 10/1986 | Eisenloeffel | E21B 17/046 175/320 |
| 5,137,398 A | * | 8/1992 | Omori | B23B 51/048 175/420.2 |
| 5,330,480 A | * | 7/1994 | Meloul | A61B 17/1617 606/170 |

(Continued)

FOREIGN PATENT DOCUMENTS

JP 2014-511194 A 5/2014
KR 20-0300750 Y1 1/2003
(Continued)

*Primary Examiner* — David W Bates
(74) *Attorney, Agent, or Firm* — IP Legal Services, LLC

(57) ABSTRACT

A detachable medical cutting tool includes a shank portion, a cutting edge portion, a rotation prevention portion and a coherence keeping portion. The shank portion includes a connection portion. The cutting edge portion includes a combination portion to be combined removably with the connection portion of the shank portion. The rotation prevention portion is interposed between the connection portion of the shank portion and the combination portion of the cutting edge portion. The rotation prevention portion prevents from a rotation in a rotation direction. The coherence keeping portion keeps coherence when the connection portion of the shank portion and the combination portion of the cutting edge portion are combined with each other. The shank portion includes stainless steel. The cutting edge portion includes zirconia. The detachable medical cutting tool is configured to be combined with a high speed rotation apparatus to perform a perforation drilling at a bone tissue of a human body.

15 Claims, 14 Drawing Sheets

(56) References Cited

U.S. PATENT DOCUMENTS

| | | | | |
|---|---|---|---|---|
| 5,400,861 A | * | 3/1995 | Sheirer | E21B 10/38 175/427 |
| 5,499,984 A | * | 3/1996 | Steiner | A61B 17/164 408/713 |
| 5,522,817 A | * | 6/1996 | Sander | A61B 17/0642 606/329 |
| 5,927,411 A | * | 7/1999 | Sheirer | E21B 17/03 175/320 |
| 7,419,017 B2 | * | 9/2008 | Walker | E21B 10/62 175/413 |
| 2002/0159851 A1 | * | 10/2002 | Krenzer | B23B 51/02 408/230 |
| 2005/0216013 A1 | * | 9/2005 | Dallara | A61B 17/1617 606/198 |
| 2008/0262526 A1 | * | 10/2008 | Neubardt | A61B 17/1615 606/180 |
| 2011/0287386 A1 | * | 11/2011 | Better | A61C 8/0018 433/174 |
| 2013/0302748 A1 | | 11/2013 | Friedrichs | |

FOREIGN PATENT DOCUMENTS

| | | |
|---|---|---|
| KR | 20-0434629 Y1 | 12/2006 |
| KR | 10-2009-0064721 A | 6/2009 |
| KR | 10-2011-0016602 A | 2/2011 |
| KR | 10-1028889 B1 | 4/2011 |

* cited by examiner (a) (b) (c)

(d) (e) (f) (g)

(a)

(b)

DETACHABLE MEDICAL CUTTING TOOL

CROSS-REFERENCE TO RELATED APPLICATION

This application claims priority under 35 USC § 119 to Korean Patent Application No. 10-2016-0033403 filed on Mar. 21, 2016 and Korean Patent Application No. 10-2016-0033421 filed on Mar. 21, 2016 in the Korean Intellectual Property Office (KIPO), the entire disclosure of which is incorporated by reference herein.

BACKGROUND

1. Field

Example embodiments relate to cutting tools for dentistry, general surgery, veterinary medicine, etc. More particularly, example embodiments relate to cutting tools including a shank portion and a cutting portion including a dual structure of material and composition such that material of main body is reduced, economic feasibility is enhanced, easy detachability is obtained, strong coherence is obtained in a combination mode, durability and a cutting force increase, friction heat decreases, and tissue damage by friction heat of a cutting edge portion is prevented.

2. Description of the Related Art

Recently, implant procedures in a dental procedure of a medical procedure universally are prevalent. In the implant procedures, an artificial tooth fixture having a screw shape and including titanium is implanted to be amalgamate with a bone in a region at which a tooth is removed, and then a connection member such as an abutment is combined, and then a prosthetic appliance such as a crown is fixed such that an original ability of a tooth is recovered.

FIG. 1 is a cross-sectional view illustrating an example of a conventional medical cutting tool.

As illustrated in FIG. 1, a perforation drill 1 is used in an implant dental procedure to perforate an alveolar bone to implant an artificial tooth.

In using the conventional perforation drill 1 having a metal material, the perforation drill 1 having a proper diameter corresponding to an implant procedure situation must be used and a perforation procedure must be operated carefully such that a damage of a bone tissue by a friction heat is prevented. In the perforation procedure, when the friction heat at a cutting edge portion 3 increases, a bone tissue of a tooth is damaged by the friction heat. The friction heat must be less than a human temperature such that easy osseointegration after an implantation at the alveolar bone is obtained.

Conventionally, a rotation RPM (rotation per minute) of a cutting tool is controlled to reduce the friction heat. In a first step of a perforation procedure by using a perforation drill, a perforation hole is made at an implant region at a rotation RPM which is within a range of about 1000 RPM to about 1500 RPM under 35 NCm torque, and in a second step, another perforation drill of which diameter is substantially greater than a diameter of the perforation drill is used at a rotation RPM which is within a range of about 500 RPM to about 800 RPM or about 300 RPM to about 400 RPM to reduce the friction heat.

However, the implant procedure depends on a personal skill of an operator, and the bone tissue is damaged by the friction heat such that it results in a bad osseointegration of an implant.

In the conventional perforation procedure, a coolant such as a cool saline solution is sprayed to reduce the friction heat of the cutting tool.

However, the saline solution as the coolant and a powder generated in the perforation procedure can be swallowed by a patient such that the use of the saline solution is limited and the friction heat of the cutting edge portion 3 cannot be cooled enough.

The cutting tool such as the perforation drill in the conventional implant procedure includes a stainless steel (medical grade) drill which is not rusty and hygienic. However, by a high thermal conductivity of the cutting tool such as the stainless steel (medical grade) drill, a friction heat greater than a human temperature is generated when an implant or an fixture is inserted in the alveolar bone, and then the coolant is necessary in the implant procedure.

When the cutting tool such as the stainless steel (medical grade) drill is used in the implant procedure, the friction heat at a high temperature can be transferred into a neuron of the alveolar bone and a necrosis of the neuron occurs. A bad osseointegration and loosening after the implant procedure can occur.

Though the stainless steel (medical grade) drill as the convention cutting tool is hygienic, a surface of the cutting tool becomes rusty by frequent cleaning and disinfection due to repeated use. Some patients may have an allergy to a metal material such as stainless steel (medical grade). Additionally, by the high thermal conductivity of the stainless steel (medical grade) drill, though the saline solution is used as a coolant, the friction heat is not cooled easily such that a bone tissue is damaged by the friction heat.

In order to solve the problems, instead of the stainless steel (medical grade) drill, a zirconia (ceramic) drill is used in the implant procedure, recently.

The zirconia (ceramic) drill has chemical resistance, corrosion resistance and bioaffinity such that a side affect such as an allergy to a metal material does not occur. And a perforation procedure by using the zirconia (ceramic) drill has a high cut efficiency and a low friction coefficient such that a lower friction heat than a friction heat by the stainless steel (medical grade) drill is generated and a perforation procedure without a coolant is possible.

However, the conventional zirconia (ceramic) drill is brittle. Particularly, a shank portion and a cutting edge portion is manufactured integrally such that the shank portion is easily broken when the shank portion is connected to a handpiece of the high speed rotation apparatus or when the shank portion is rotated at a high RPM, and a boundary between the shank portion and the cutting edge portion is broken.

Additionally, the conventional zirconia (ceramic) drill is manufactured by a powder compression sintering method such that a manufacture cost is high and the use of the integrated zirconia (ceramic) drill is limited. In a dental clinic, the use of the zirconia (ceramic) drill of which cost is greater than a cost of the stainless steel (medical grade) drill is avoided, and it is difficult that the zirconia (ceramic) drill having much advantage is distributed widely.

Korean Utility Registration No. 20-0434629 and Korean Utility Registration No. 20-0300750 are prior arts.

Accordingly, a new dental cutting tool having a low friction heat and a high durability is needed.

SUMMARY

Example embodiments provide a detachable medical cutting tool including a shank portion and a cutting portion including a dual structure of material and composition such that material of main body is reduced, economic feasibility is enhanced, easy detachability is obtained, strong coherence is obtained in a combination mode Example embodiments provide a detachable medical cutting tool having a high durability and a high cutting force such that friction heat decreases and tissue damage by friction heat of a cutting edge portion is prevented.

According to example embodiments, there is provided a detachable medical cutting tool. The detachable medical cutting tool includes a shank portion, a cutting edge portion, a rotation prevention portion and a coherence keeping portion. The shank portion includes a connection portion. The cutting edge portion includes a combination portion to be combined removably with the connection portion of the shank portion. The rotation prevention portion is interposed between the connection portion of the shank portion and the combination portion of the cutting edge portion. The rotation prevention portion prevents from a rotation in a rotation direction. The coherence keeping portion keeps coherence when the connection portion of the shank portion and the combination portion of the cutting edge portion are combined with each other. The shank portion includes stainless steel (medical grade). The cutting edge portion includes zirconia. The detachable medical cutting tool is configured to be combined with a high speed rotation apparatus to perform a perforation drilling at a bone tissue of a human body.

In example embodiments, the coherence keeping portion may include a combination groove, a combination protrusion, a coherence keeping member and an installation groove. The combination groove may be arranged in one of the connection portion of the shank portion and the combination portion of the cutting edge portion. The combination protrusion may be arranged at the other of the connection portion of the shank portion and the combination portion of the cutting edge portion. The combination protrusion may have a cross-sectional shape corresponding to a cross-sectional shape of the combination groove. The coherence keeping member may be installed on one of the combination groove and the combination protrusion. The installation groove may be arranged at the other of the combination groove and the combination protrusion, the coherence keeping member installed on the installation groove.

In example embodiments, the coherence keeping member may include a C-ring, an O-ring or a cut annular ring. A portion of the cut annular ring may be removed, and ends of the cut annular ring may be crossed.

In example embodiment, an outer diameter of the C-ring or the cut annular ring may be substantially greater than an inner diameter of the combination groove when the coherence keeping member includes the C-ring or the cut annular ring.

In example embodiments, an inner diameter of the C-ring or the cut annular ring may be substantially less than an outer diameter of the combination protrusion when the coherence keeping member includes the C-ring or the cut annular ring.

In example embodiments, the combination protrusion may be narrowed and tapered toward an end. The combination groove may be tapered corresponding to the combination protrusion. The installation groove may be arranged in an inner surface of the combination groove.

In example embodiments, the coherence keeping member may include a C-ring, an O-ring or a cut annular ring. A portion of the cut annular ring may be removed, and ends of the cut annular ring may be crossed. The C-ring, the O-ring or the cut annular ring may have a round stepped cross-sectional shape with two stages.

In example embodiments, an elastic force may be applied to the C-ring, the O-ring or the cut annular ring toward one side or the other side in a plan view.

In example embodiments, the coherence keeping member may include a leaf spring having an annular shape. A first jagged portion may having a sawtooth shape may be arranged at an inner surface of the C-ring or the cut annular ring when the C-ring or the cut annular ring is installed on the combination protrusion. A second jagged portion having a sawtooth shape may be arranged at an installation surface of the combination protrusion on which the C-ring or the cut annular ring is installed.

In example embodiments, the one of the connection portion of the shank portion and the combination portion of the cutting edge portion may be divided into more than two pieces. The combination groove may have a linear shape or a tapered shape in a cross-sectional view.

In example embodiments, the detachable medical cutting tool may further include a fixing portion to fix the combination portion to the connection portion. The fixing portion may include a combination hole having an inner screw thread and a combination member screw-combined with the combination hole. The combination hole may penetrate the combination groove in a perpendicular direction to the combination groove.

According to example embodiments, there is provided a detachable medical cutting tool. The detachable medical cutting tool includes a shank portion, a cutting edge portion, a rotation prevention portion and a combination part. The shank portion includes a connection portion. The cutting edge portion includes a combination portion to be combined removably with the connection portion of the shank portion. The rotation prevention portion may be interposed between the connection portion of the shank portion and the combination portion of the cutting edge portion. The rotation prevention portion prevents from a rotation in a rotation direction. The combination part combines the cutting edge portion with the shank portion removably. The shank portion includes stainless steel. The cutting edge portion may include zirconia. The detachable medical cutting tool is configured to be combined with a high speed rotation apparatus to perform a perforation drilling at a bone tissue of a human body.

In example embodiments, the combination part may include a combination groove, a combination protrusion and a fixing portion. The combination groove may be arranged in one of the connection portion of the shank portion and the combination portion of the cutting edge portion. The combination protrusion may be arranged at the other of the connection portion of the shank portion and the combination portion of the cutting edge portion. The combination protrusion may be inserted in the combination groove. The fixing portion may fix the combination portion to the connection portion. The fixing portion may include a combination hole, a fix hole and a combination member. The combination hole may have an inner screw thread. The combination hole may penetrate the combination groove in a perpendicular direction to the combination groove. The fix hole may penetrate the combination protrusion in a perpendicular direction to the combination protrusion. The combination member may be fixed to the fix hole through the combination hole.

In example embodiments, the detachable medical cutting tool may further include a position marker at an outer surface of the cutting edge portion in a virtual extension line crossing a center of the fix hole to represent a position of the fix hole.

In example embodiments, the combination protrusion may include an annular groove. The combination member may include a stripper bolt. The combination surface having a round waveform corresponding to an outer surface of the stripper bolt may be formed at each of top and bottom surfaces of the annular groove.

In example embodiments, the combination part may include a combination groove, a combination protrusion and a fixing portion. The combination groove may be arranged in one of the connection portion of the shank portion and the combination portion of the cutting edge portion. The combination protrusion may be arranged at the other of the connection portion of the shank portion and the combination portion of the cutting edge portion. The combination protrusion may be inserted in the combination groove. The fixing portion may fix the combination portion to the connection portion. The fixing portion may include a combination hole, a combination carrier portion and a combination member. The combination hole may have an inner screw thread. The combination hole may penetrate the combination groove in a perpendicular direction to the combination groove. The combination carrier portion may be interposed between the combination groove and the combination protrusion to increase a combination area. The combination member may be combined with the combination carrier portion through the combination hole.

In example embodiments, the combination carrier portion may include an annular groove, a ring member, a penetration hole and a friction growth portion. The annular groove may be arranged at the combination protrusion. The ring member may be installed at the annular groove. The penetration hole may be arranged at the ring member. The friction growth portion may be interposed between the annular groove and the ring member.

In example embodiments, the friction growth portion may include a first jagged portion and a second jagged portion. The first jagged portion may be arranged at the annular groove, the jagged portion having a sawtooth shape. The second jagged portion may be arranged in an inner surface of the ring member and having a sawtooth shape. The second jagged portion may correspond to the first jagged portion.

In example embodiments, the rotation prevention portion may be arranged at each of an end of the connection portion and an end of the combination portion. The rotation prevention portion may have an elliptical shape, a polygonal shape or a jagged sawtooth shape in a cross-sectional view.

BRIEF DESCRIPTION OF THE DRAWINGS

Example embodiments will be more clearly understood from the following detailed description taken in conjunction with the accompanying drawings.

FIG. 1 is a cross-sectional view illustrating an example of a conventional medical cutting tool.

FIG. 2 is a view illustrating a detachable medical cutting tool in accordance with a first embodiment.

FIG. 3 is a plan view illustrating a rotation prevention portion of FIG. 1 in accordance with the first embodiment.

FIG. 4 is a plan view illustrating a coherence keeping portion of FIG. 1 in accordance with example embodiments.

FIG. 5 is a plan view illustrating a coherence keeping portion of FIG. 1 in accordance with example embodiments.

FIG. 6 is a view illustrating a detachable medical cutting tool in accordance with a second embodiment.

FIG. 7 is a view illustrating a detachable medical cutting tool in accordance with a third embodiment.

FIG. 8 is a cross-section view illustrating a combination relation of the detachable medical cutting tool of FIG. 7 in accordance with the third embodiment.

FIG. 9 is a plan view illustrating a coherence keeping member of FIG. 7 in accordance with the third embodiment and a side view illustrating a coherence keeping member of FIG. 8.

FIG. 10 is a view illustrating a coherence keeping member and a cutting edge portion of FIG. 7 in accordance with example embodiments.

FIG. 11 is a view illustrating a detachable medical cutting tool in accordance with a fourth embodiment.

FIG. 12 is a view illustrating a portion of the detachable medical cutting tool of FIG. 11. In accordance with the fourth embodiment.

FIG. 13 is a disassembled perspective view illustrating a detachable medical cutting tool in accordance with a fifth embodiment.

FIG. 14 is a view illustrating a combination portion of the detachable medical cutting tool of FIG. 13 in accordance with example embodiment.

FIG. 15 is a disassembled perspective view partially illustrating a detachable medical cutting tool in accordance with a sixth embodiment.

DETAILED DESCRIPTION OF THE EMBODIMENTS

Figure 1:
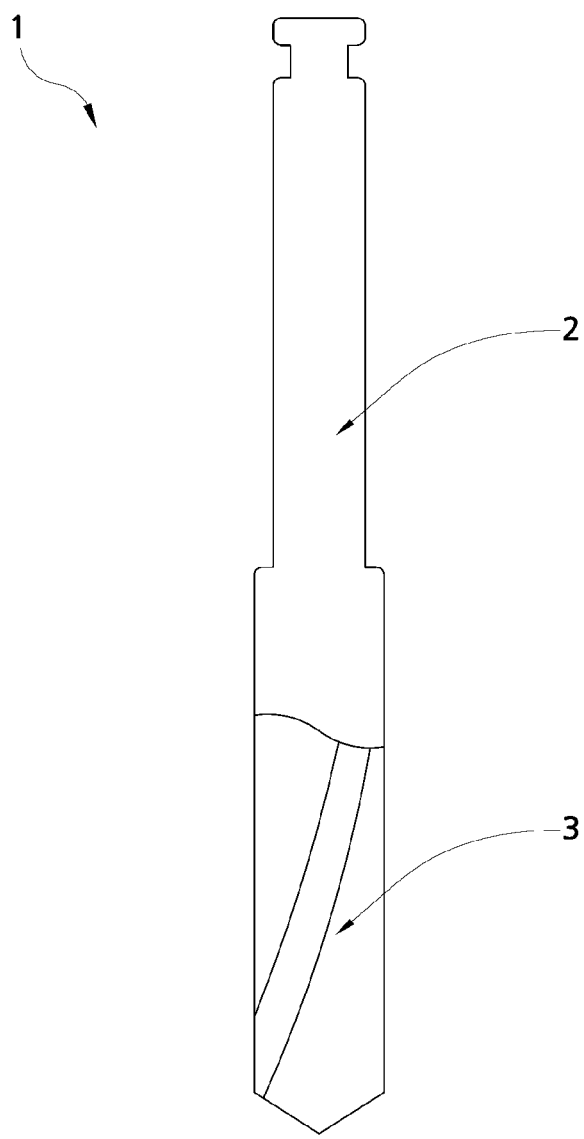
FIGS. 1 to 15 represent non-limiting, example embodiments as described herein.

Various example embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. Like numerals refer to like elements throughout.

It will be understood that, although the terms first, second, third etc. may be used herein to describe various elements, these elements should not be limited by these terms.

These terms are used to distinguish one element from another. Thus, a first element discussed below could be termed a second element without departing from the teachings of the present inventive concept. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular example embodiments only and is not intended to be limiting of the present inventive concept. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
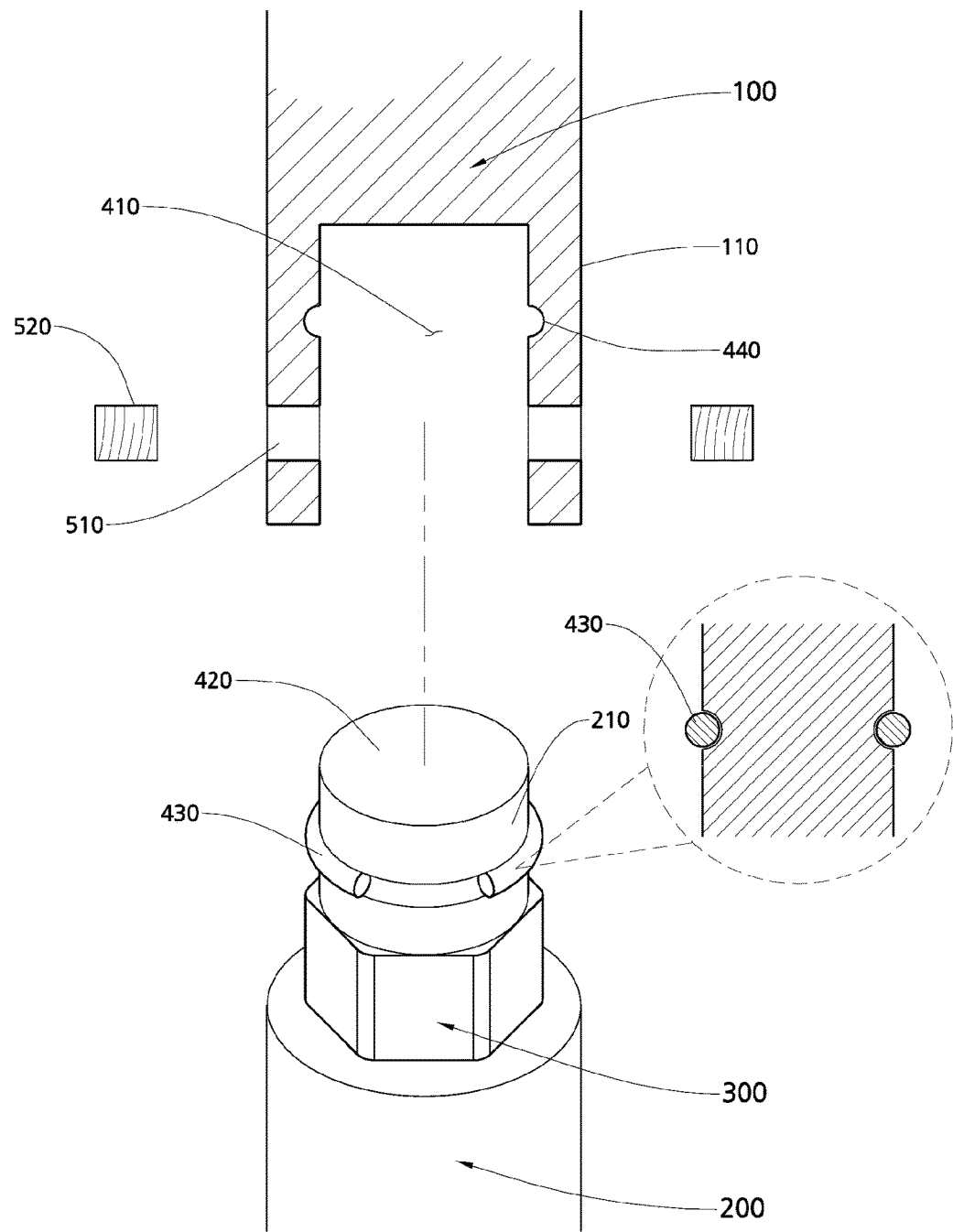
Figure 3:
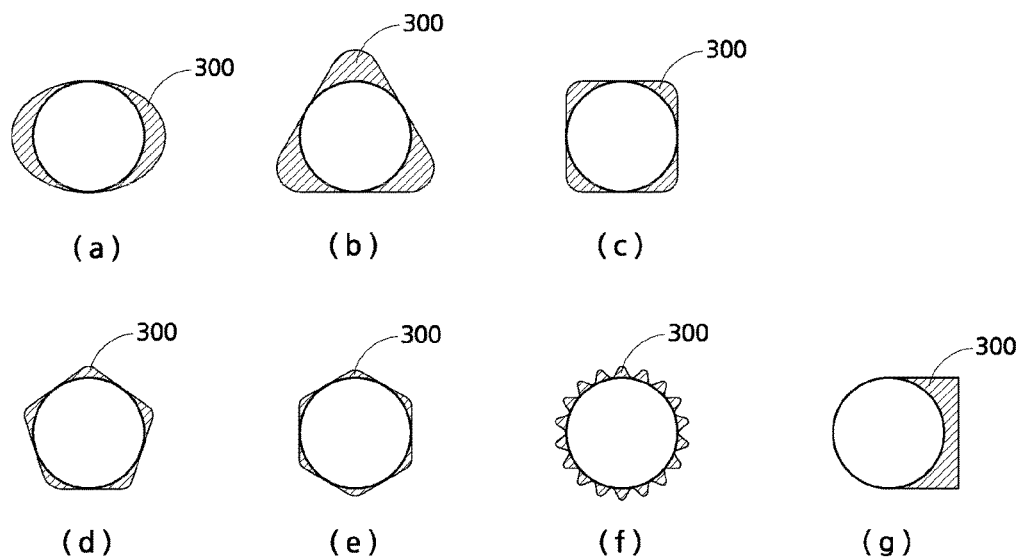
Figure 4:
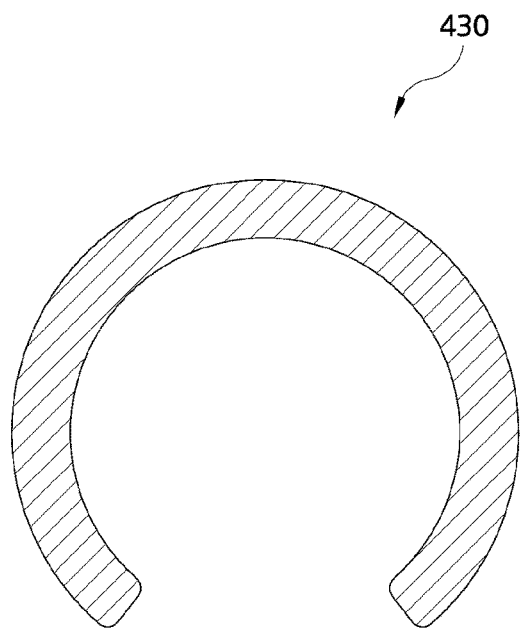
Figure 5:
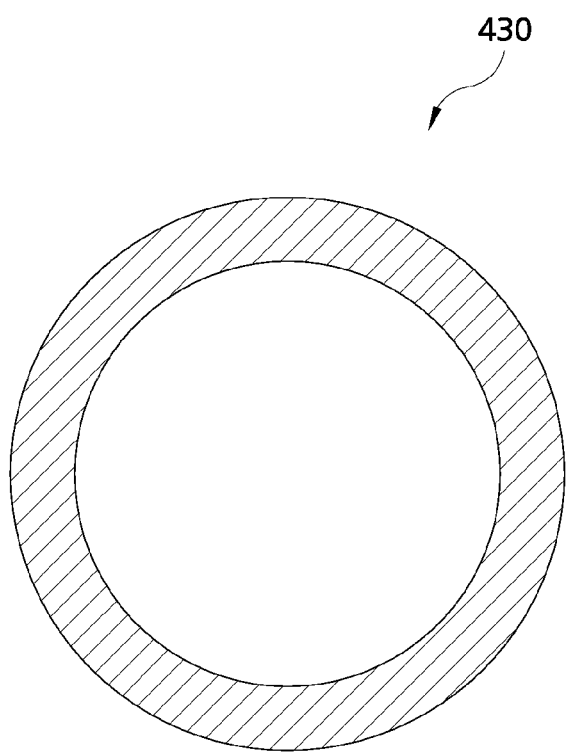

FIG. 2 is a view illustrating a detachable medical cutting tool in accordance with a first embodiment. FIG. 3 is a plan view illustrating a rotation prevention portion of FIG. 1 in accordance with the first embodiment. FIG. 4 is a plan view illustrating a coherence keeping portion of FIG. 1 in accordance with example embodiments. FIG. 5 is a plan view illustrating a coherence keeping portion of FIG. 1 in accordance with example embodiments.

As illustrated in FIGS. 2 to 5, a detachable medical cutting tool according to a first embodiment includes a shank portion 100, a cutting edge portion 200, a rotation prevention portion 300 and a coherence keeping portion. The shank portion 100 includes a connection portion 110. The cutting edge portion 200 includes a combination portion 210 to be combined removably with the connection portion 110 of the shank portion 100. A drill edge is provided at an outer surface of the cutting edge portion 200. The rotation prevention portion 300 is interposed between the connection portion 110 of the shank portion 100 and the combination portion 210 of the cutting edge portion 200. The rotation prevention portion 300 prevents from a rotation in a rotation direction. The coherence keeping portion keeps coherence when the connection portion 110 of the shank portion 100 and the combination portion 210 of the cutting edge portion 100 are combined with each other. The detachable medical cutting tool is configured to be combined with a high speed rotation apparatus to perform a perforation drilling at a bone tissue of a human body.

The shank portion 100 includes stainless steel (medical grade) such that the shank portion 100 has a high durability in repeated combination-separation process to a handpiece of the high speed rotation apparatus. Preferably, the shank portion 100 may include the stainless steel (medical grade) such as a TRIMRITE (UNS S42010). The shank portion 100 including the stainless steel (medical grade) may be not brittle and the shank portion 100 can be used during a long period when the shank portion 100 is attached or detached to the handpiece, repeatedly.

The cutting edge portion 200 includes zirconia having a high density and a low friction coefficient. Preferably, the cutting edge portion 200 may include the zirconia, stabilized zirconia or alumina. Additionally, the cutting edge portion 200 may include sintered carbide having a low friction coefficient and a high density. The zirconia developed as a new material is not brittle than ceramic of which brittleness is the greatest weakness. The cutting edge portion 200 including the zirconia, stabilized zirconia or alumina may be manufactured by a powder compression sintering method or a manufacturing method of an artificial sapphire such as a skull mult method such that the cutting edge portion 200 has a high density, a friction coefficient lower than a friction coefficient of the stainless steel (medical grade), chemical resistance, corrosion resistance and bioaffinity.

The cutting edge portion 200 having the zirconia has a high density and a low friction coefficient such that a friction heat of the cutting edge portion 200 by a perforation procedure at high speed rotation is lower than a friction heat of a cutting edge portion including the stainless steel (medical grade). Additionally, cooling process of spraying a coolant such as saline solution is not necessary and a side effect such as an allergy to a metal material in the perforation procedure at a bone tissue does not occur. In particular, for example, the friction heat cannot be transferred into a neuron of the alveolar bone and a necrosis of the neuron does not occur. A delicate and detailed perforation procedure can be performed such that a good osseointegration after the implant procedure can be expected.

The rotation prevention portion 300 preventing from a rotation in a rotation direction is interposed between the connection portion 110 of the shank portion 100 and the combination portion 210 of the cutting edge portion 200. A cross-sectional shape of a lower portion of the connection portion 110 or a lower portion of the combination portion 210 may have an elliptical shape, a circular shape or a polygonal shape.

In particular, referring to FIG. 3, the rotation prevention portion 300 may have an elliptical shape as (a) of FIG. 3, a polygonal shape such as a triangle, a square, a pentagon or a hexagon as (b) to (e) of FIG. 3, a jagged shape such as a sawtooth as (0 of FIG. 3, or a combination shape of a circle and a polygon as (g) of FIG. 5.

The combination structure having a cross-sectional shape is not limited therein. The shank portion 100 and the cutting edge portion 200 may be combined to rotate in a rotation direction together.

The coherence keeping portion may include a combination groove 410, a combination protrusion 420, a coherence keeping member 430 and an installation groove 440. The combination groove 410 may be arranged in the connection portion 110 of the shank portion 100. The combination protrusion 420 may be arranged at the combination portion 210 of the cutting edge portion 200. The combination protrusion 420 may have a cross-sectional shape corresponding to a cross-sectional shape of the combination groove 410. The coherence keeping member 430 may be installed on one of the combination groove 410 and the combination protrusion 420. The installation groove 440 may be arranged at the other of the combination groove 410 and the combination protrusion 420. The coherence keeping member 430 may be installed on the installation groove 440.

In the first embodiment, the coherence keeping member 430 may be arranged at the combination protrusion 420 near the combination portion 210, and the installation groove 440 may be arranged in the combination groove 410 near the connection portion 110.

As illustrated in FIGS. 4 and 5, the coherence keeping member 430 may include a C-ring, an O-ring or a cut annular ring. A portion of the cut annular ring may be removed, and ends of the cut annular ring may be crossed.

When the coherence keeping member 430 includes the C-ring or the cut annular ring, an elastic force is applied toward a radial direction at the C-ring or the cut annular ring. An outer diameter of the C-ring or the cut annular ring may be substantially greater than an inner diameter of the combination groove 410 such that the C-ring or the cut annular ring is installed at the combination protrusion 420.

The outer diameter of the C-ring or the cut annular ring may be substantially greater than the inner diameter of the combination groove 410, and the C-ring or the cut annular ring is installed at the combination protrusion 420 such that the C-ring or the cut annular ring may be shrunken during a combination process of the connection portion 110 and the combination portion 210, and the C-ring or the cut annular ring may be extended and restored to an original position when the connection portion 110 and the combination portion 210 are completely combined such that the C-ring or the cut annular ring may be installed at the combination groove 410.

Figure 6:
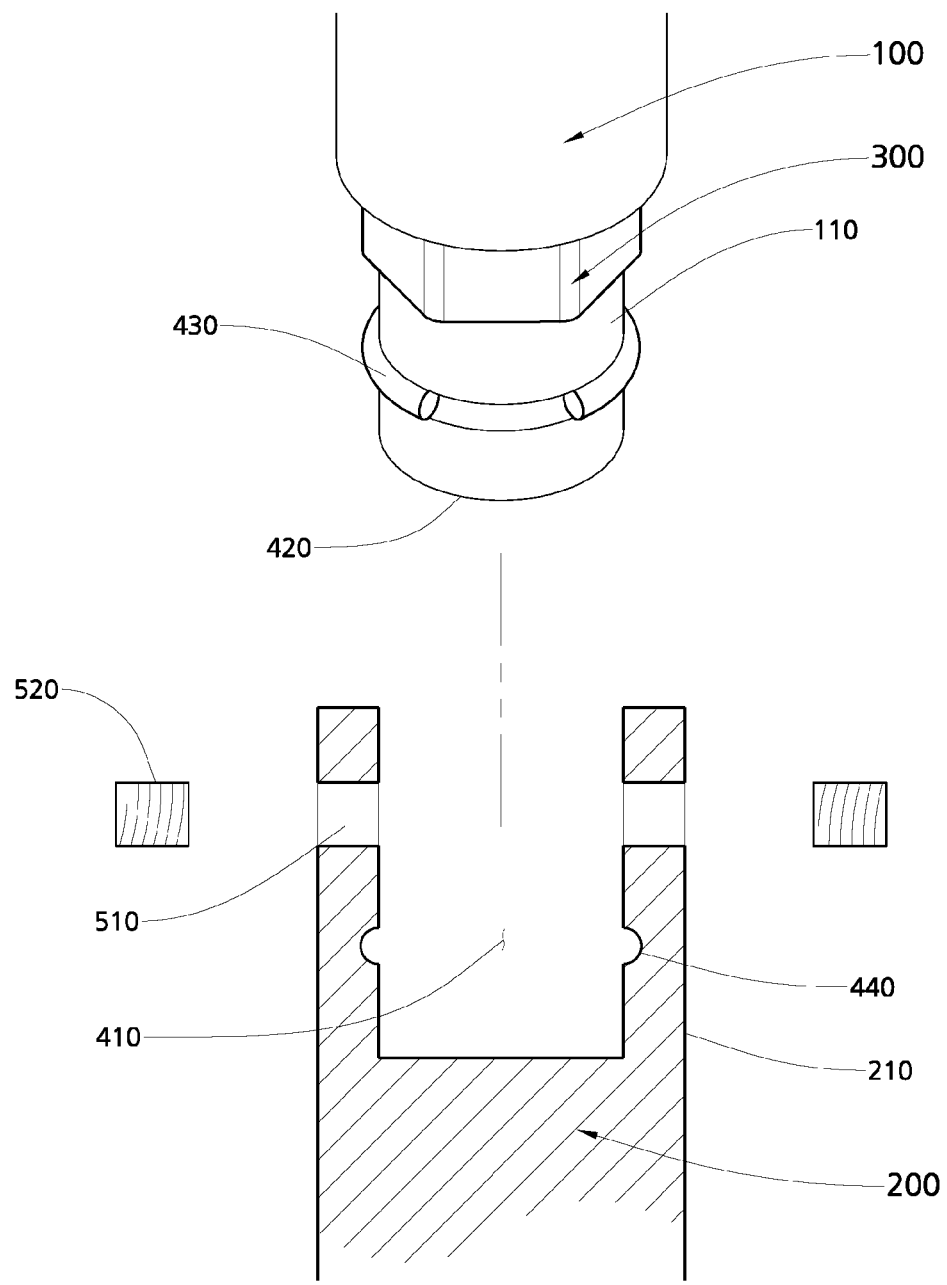

FIG. 6 is a view illustrating a detachable medical cutting tool in accordance with a second embodiment. The detachable medical cutting tool is substantially the same as or similar to that of FIGS. 2 to 5 except for a coherence keeping portion in a combination between a connection portion of a shank portion and a combination portion of a cutting edge portion. Thus, the same or like reference numerals will be used to refer to the same or like elements and any further repetitive explanation concerning the above elements will be omitted.

As illustrated in FIG. 6, a coherence keeping portion of a detachable medical cutting tool in accordance with a second embodiment may include a combination protrusion 420, a combination groove 410, a coherence keeping member 430 and an installation groove 440.

The combination protrusion 420 may be arranged at a connection portion 110 of a shank portion 100. The combination groove 410 may be arranged in a combination portion 210 of a cutting edge portion 200. The combination groove 410 may have a cross-sectional shape corresponding to a cross-sectional shape of the combination protrusion 420. The coherence keeping member 430 may be installed on one of the combination groove 410 and the combination protrusion 420. The installation groove 440 may be arranged at the other of the combination groove 410 and the combination protrusion 420. The coherence keeping member 430 may be installed on the installation groove 440.

In the second embodiment, the coherence keeping member 430 may be arranged at the combination protrusion 420 near the connection portion 110, and the installation groove 440 may be arranged at the combination groove 410 near the combination portion 210.

The coherence keeping member 430 may include a C-ring, an O-ring, or a cut annular ring as like the first embodiment.

When the coherence keeping member 430 includes the C-ring or the cut annular ring, an elastic force is applied toward a radial direction at the C-ring or the cut annular ring. An outer diameter of the C-ring or the cut annular ring may be substantially greater than an inner diameter of the combination groove 410 such that the C-ring or the cut annular ring is installed at the combination protrusion 420.

Although the figures of the first and second embodiments illustrate that the C-ring or the cut annular ring is installed on the combination protrusion 420, the C-ring or the cut annular ring may be installed on the combination groove 410. An inner diameter of the C-ring or the cut annular ring may be substantially less than an outer diameter of the combination protrusion 420 such that the C-ring or the cut annular ring may be installed at the combination groove 410.

The inner diameter of the C-ring or the cut annular ring may be substantially less than the outer diameter of the combination protrusion 420, and the C-ring or the cut annular ring is installed at the combination groove 410 such that the C-ring or the cut annular ring may be extended during a combination process of the connection portion 110 and the combination portion 210, and the C-ring or the cut annular ring may be shrunken and restored to an original position when the connection portion 110 and the combination portion 210 are completely combined such that the C-ring or the cut annular ring may be installed at the combination protrusion 420.

Figure 7:
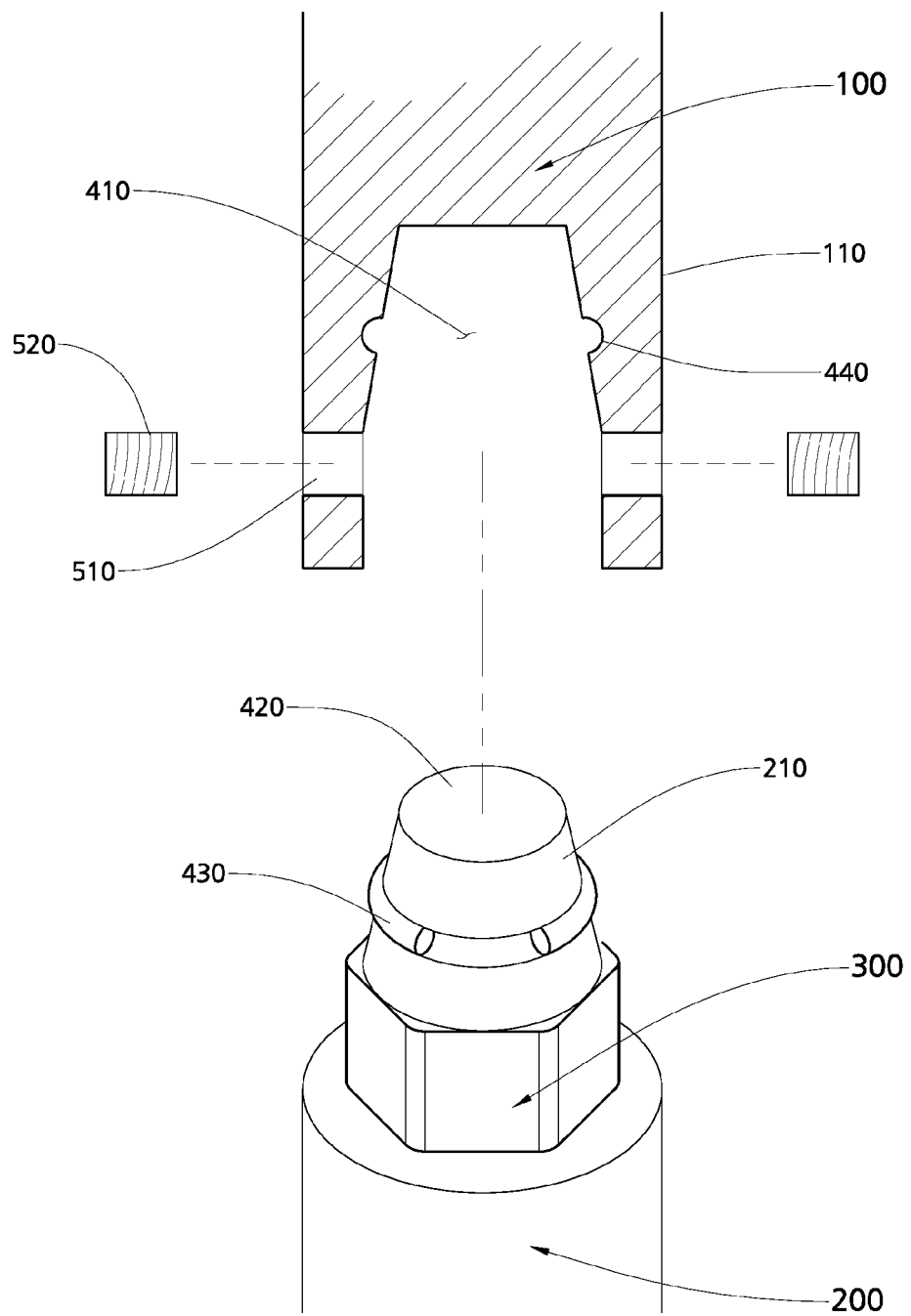
Figure 8:
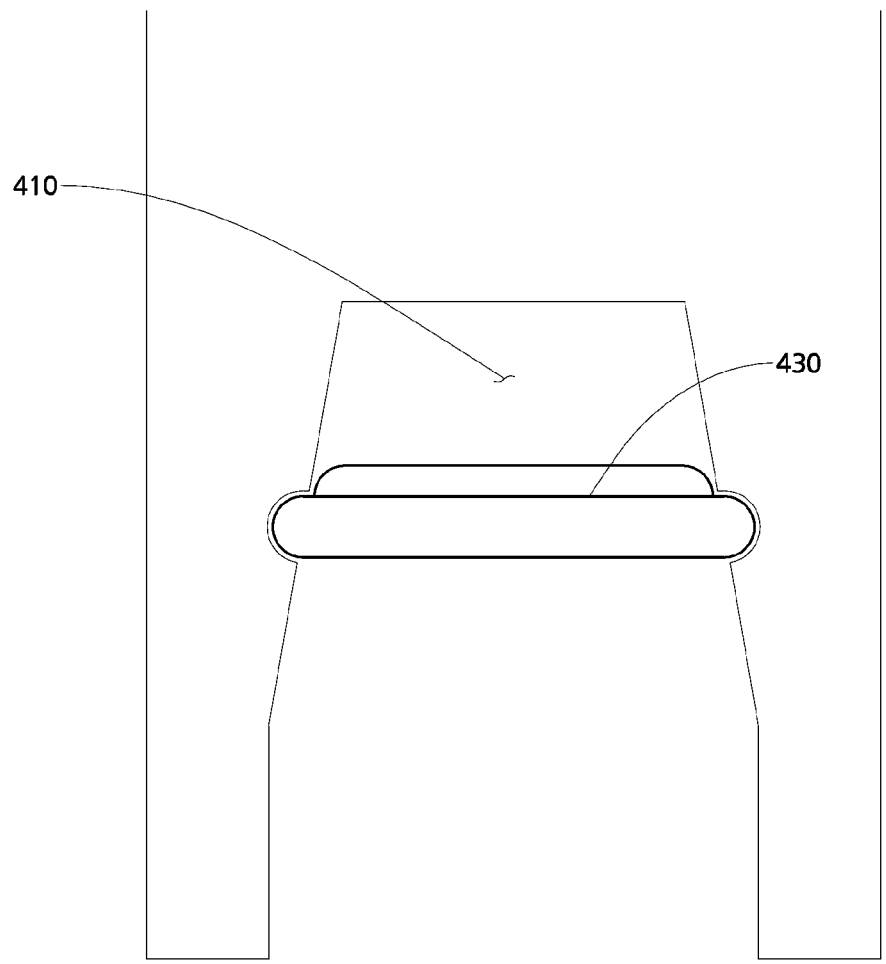
Figure 9:
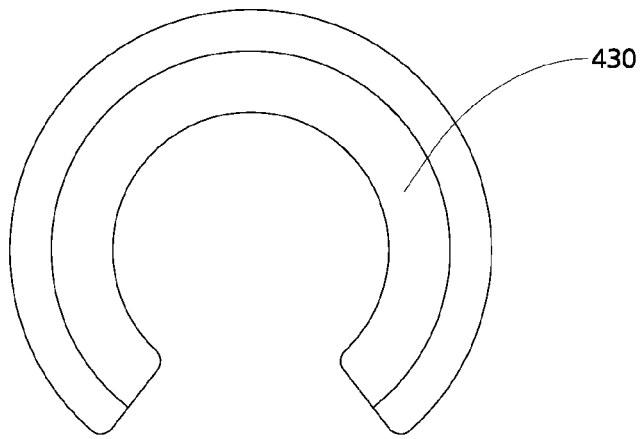
Figure 9:
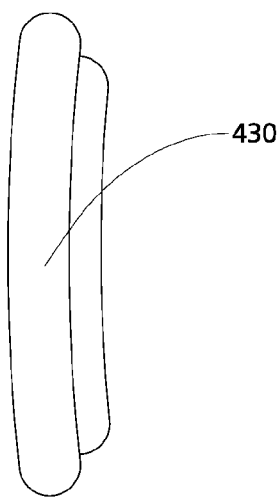
Figure 10:
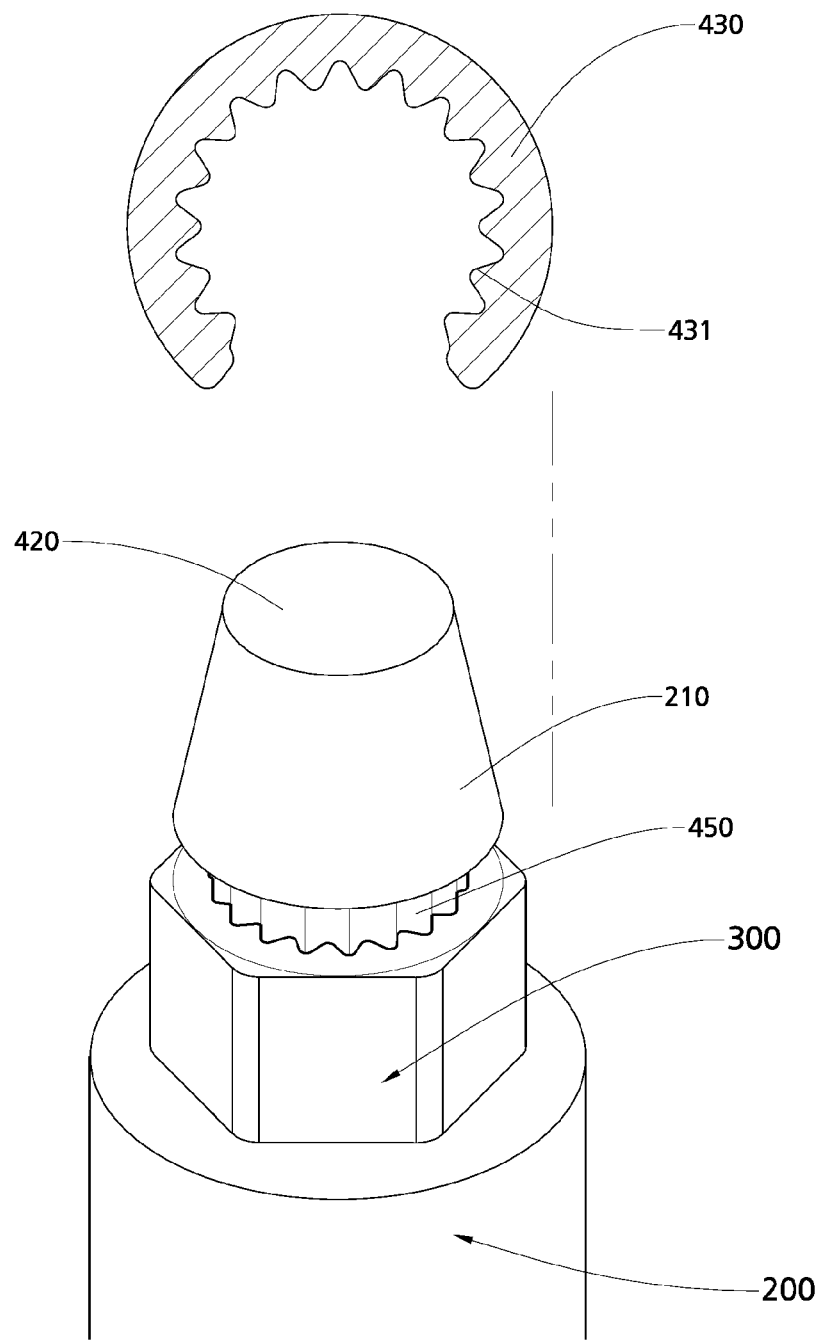

FIG. 7 is a view illustrating a detachable medical cutting tool in accordance with a third embodiment. FIG. 8 is a cross-section view illustrating a combination relation of the detachable medical cutting tool of FIG. 7 in accordance with the third embodiment. FIG. 9 is a plan view illustrating a coherence keeping member of FIG. 7 in accordance with the third embodiment and a side view illustrating a coherence keeping member of FIG. 8. FIG. 10 is a view illustrating a coherence keeping member and a cutting edge portion of FIG. 7 in accordance with example embodiments.

The detachable medical cutting tool is substantially the same as or similar to that of FIGS. 2 to 5 except for a coherence keeping portion in a combination between a connection portion of a shank portion and a combination portion of a cutting edge portion. Thus, the same or like reference numerals will be used to refer to the same or like elements and any further repetitive explanation concerning the above elements will be omitted.

As illustrated in FIGS. 7 to 9, a coherence keeping portion of a detachable medical cutting tool in accordance with a third embodiment may include a combination groove 410, a combination protrusion 420, a coherence keeping member 430 and an installation groove 440. The combination groove 410 may be arranged in a connection portion 110 of a shank portion 100. The combination protrusion 420 may be arranged at a combination portion 210 of a cutting edge portion 200. The combination protrusion 420 may have a cross-sectional shape corresponding to a cross-sectional shape of the combination groove 410. The coherence keeping member 430 may be installed on one of the combination groove 410 and the combination protrusion 420. The installation groove 440 may be arranged at the other of the combination groove 410 and the combination protrusion 420. The coherence keeping member 430 may be installed on the installation groove 440. The combination protrusion 420 may be narrowed and tapered toward a combination, and the combination groove 410 may be tapered corresponding to the combination protrusion 420.

In the third embodiment, the coherence keeping member 430 may be arranged at the combination protrusion 420 near the combination portion 210, and the installation groove 440 may be arranged in the combination groove 410 near the connection portion 110.

The coherence keeping member 430 may include a C-ring, an O-ring or a cut annular ring as like the first embodiment. In the third embodiment, a radius of curvature of one end of the C-ring or the cut annular ring and a radius of curvature of the other end of the C-ring or the cut annular ring may be different from each other. The C-ring or the cut annular ring may have a two-stage structure having diameters different from each other. The C-ring or the cut annular ring may have a round stepped cross-sectional shape with two stages, and the installation groove 440 at which the C-ring or the cut annular ring is installed may have a cross-sectional shape corresponding thereto. The C-ring or the cut annular ring may have a round stepped cross-sectional shape with two stages such that combination ability in a combination direction is obtained and a strong coherence in a perpendicular direction to the combination direction is also obtained.

Additionally, an elastic force is applied by the C-ring or the cut annular ring in a side direction in a plan view, eccentrically. For example, the coherence keeping member may include a C-ring of a leaf spring, a cut annular ring of a leaf spring or an O-ring of a leaf spring.

Accordingly, the elastic force is applied in the side direction (a shank portion direction) by the C-ring or the cut annular ring, eccentrically, such that the C-ring or the cut annular ring may be moved in an opposite direction of the combination direction by a friction force during a combination process of the C-ring or the cut annular ring, and the C-ring or the cut annular ring may be restored to an original position by an elastic restoring force when the combination process is concluded. An operator may feel like a sense of a restoration click of the C-ring or the cut annular ring such that the operator knows that stable combination is obtained. Additionally, when the operator performs a procedure in an eccentrical situation of the C-ring or the cut annular ring, an elastic force by an eccentricity may be applied in a perforation direction such that a buffer is served during the procedure, the procedure is easy and pain of a patient decreases.

These constructive features may be applied to the embodiments previously described or embodiments described later.

Although the combination protrusion 420 may be arranged near the combination portion 210 of the cutting edge portion 200 and the combination groove 410 may be arranged near the connection portion 110 of the shank portion 100 in the third embodiment, an opposition composition is possible and a shrinkage elastic force or an extension elastic force is applied according a arrangement of the C-ring or the cut annular ring.

In particular, when the C-ring or the cut annular ring is arranged at the combination protrusion 420, an outer diameter of the C-ring or the cut annular ring may be substantially greater than an inner diameter of the installation groove 440 such that the C-ring or the cut annular ring may be installed at the combination protrusion 420. When the C-ring or the cut annular ring is arranged at the combination groove 410, an inner diameter of the C-ring or the cut annular ring may be substantially less than an outer diameter of the combination protrusion 420 such that the C-ring or the cut annular ring may be installed at the combination groove 410.

Referring to FIG. 10, when the C-ring or the cut annular ring is arranged at the combination protrusion 420, a first jagged portion 431 having a sawtooth shape may be arranged at an inner surface of the C-ring or the cut annular ring. A second jagged portion 450 having a sawtooth shape corresponding thereto may be arranged at an installation surface of the combination protrusion 420 at which the C-ring or the cut annular ring is installed.

Accordingly, a strong coherence force between the coherence keeping member 430 and the combination protrusion 420 may be maintained. These constructive features may be applied when the coherence keeping member 430 is installed at the combination groove 440. When the coherence keeping member 430 is installed at the combination groove 440, a jagged portion having a sawtooth shape may be arranged at an outer surface of the coherence keeping member 430 and another jagged portion having a sawtooth shape corresponding thereto may be arranged an inner surface of the combination groove 440. These features may be applied to other embodiments.

Figure 11:
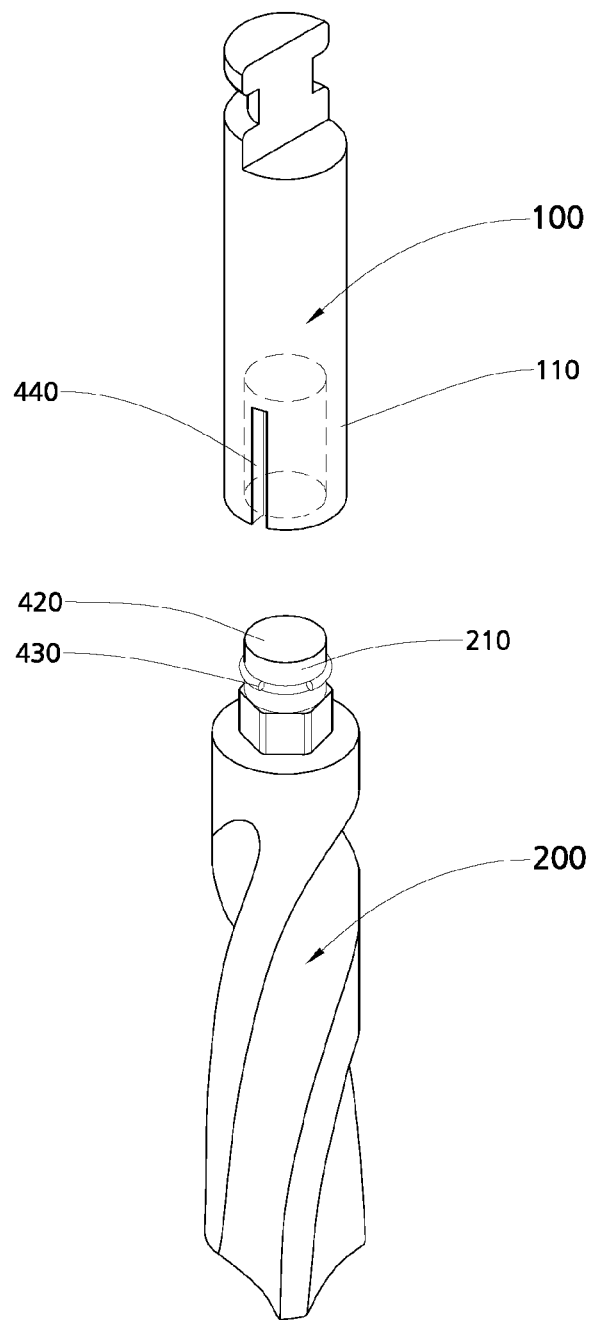
Figure 12:
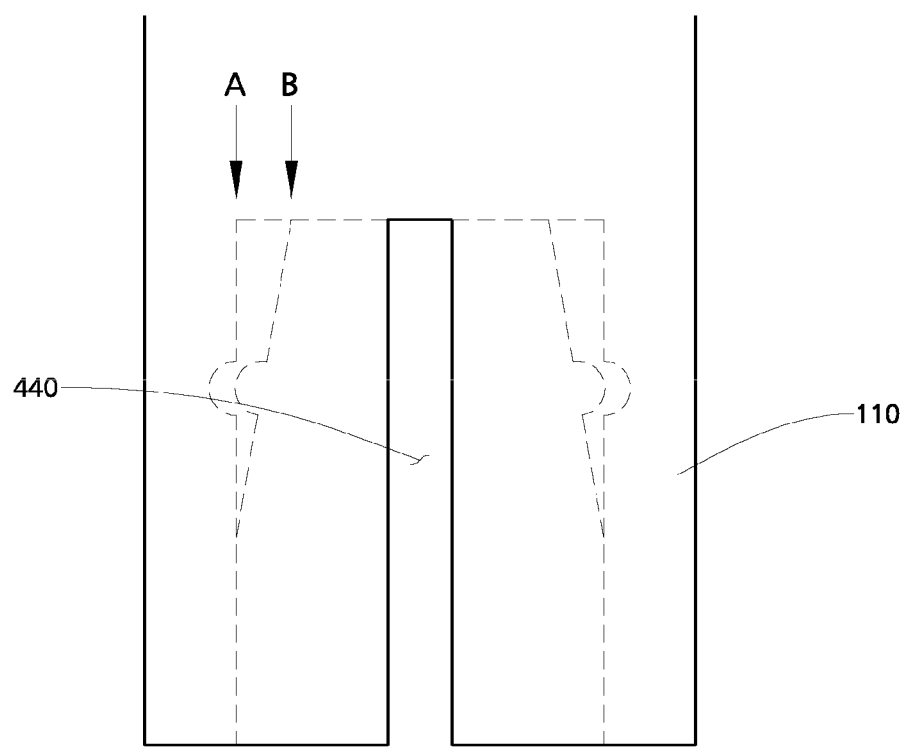

FIG. 11 is a view illustrating a detachable medical cutting tool in accordance with a fourth embodiment. FIG. 12 is a view illustrating a portion of the detachable medical cutting tool of FIG. 11. In accordance with the fourth embodiment, The detachable medical cutting tool is substantially the same as or similar to that of FIGS. 2 to 5 except for a coherence keeping portion in a combination between a connection portion of a shank portion and a combination portion of a cutting edge portion. Thus, the same or like reference numerals will be used to refer to the same or like elements and any further repetitive explanation concerning the above elements will be omitted.

As illustrated in FIGS. 11 and 12, a coherence keeping portion of a detachable medical cutting tool in accordance with a fourth embodiment may include a combination groove 410, a combination protrusion 420, a coherence keeping member 430 and an installation groove 440. The combination groove 410 may be arranged in a connection portion 110 of a shank portion 100. The combination protrusion 420 may be arranged at a combination portion 210 of a cutting edge portion 200. The combination protrusion 420 may have a cross-sectional shape corresponding to a cross-sectional shape of the combination groove 410. The coherence keeping member 430 may be installed on one of the combination groove 410 and the combination protrusion 420. The installation groove 440 may be arranged at the other of the combination groove 410 and the combination protrusion 420. The coherence keeping member 430 may be installed on the installation groove 440. The connection portion 110 at which the combination groove 410 is arranged may be divided into more than two pieces.

As illustrated in FIG. 12, the combination groove 410 arranged at the connection portion 110 may have a vertical line shape as like "A" of FIG. 12 or the combination groove 410 may have a tapered line shape as like "B" of FIG. 12. A cross-sectional shape of the combination protrusion 420 may correspond to a cross-sectional shape of the combination groove 410.

Although a respective one of the shank portion 100 and the cutting edge portion 200 may include a respective one of the connection portion 110 and the combination portion 210 in the fourth embodiment, an opposition combination may be possible and these constructive features may be applied to other embodiment.

A detachable medical cutting tool may further include a fixing portion to fix the combination portion 210 to the connection portion 110.

As illustrated in FIGS. 2, 6 and 7, the fixing portion may include a fix hole 510 and a combination member 520. The combination hole 510 may have an inner screw thread. The combination hole 510 may penetrate the combination groove 440 in a perpendicular direction to the combination groove 440 from an outer surface of the connection portion 110 of the shank portion 100. The combination member 520 may fix the combination protrusion 420 to the shank portion 100 through the combination hole 510.

Figure 13:
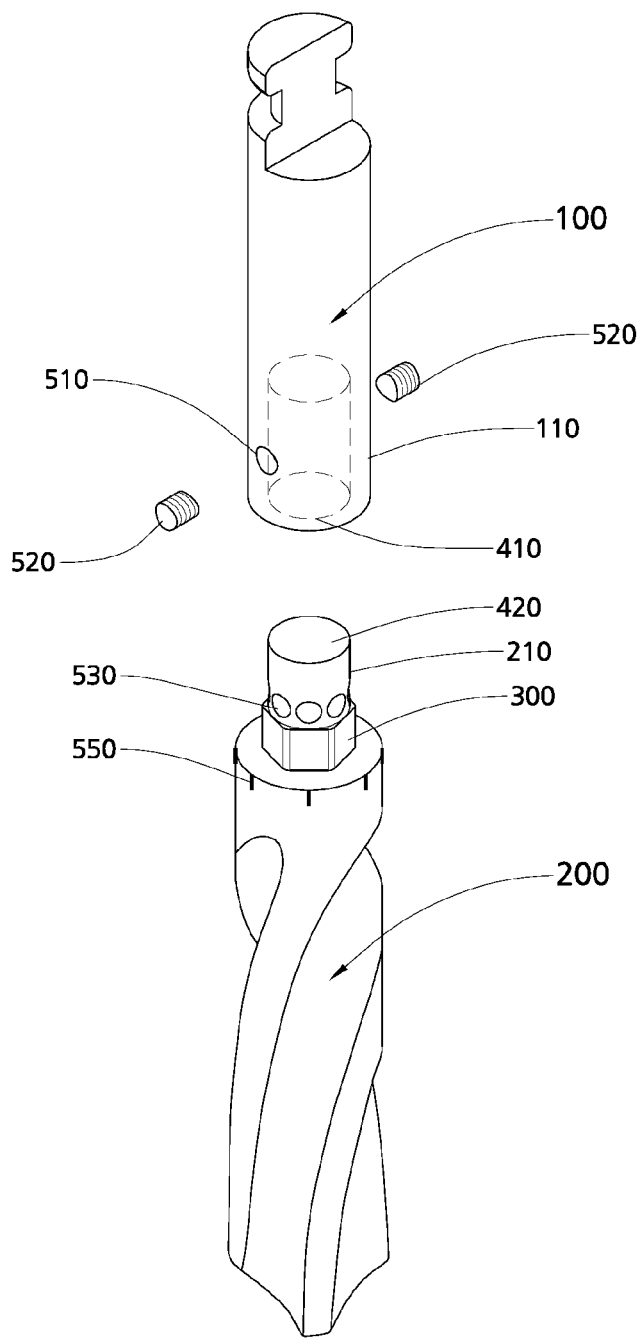
Figure 14:
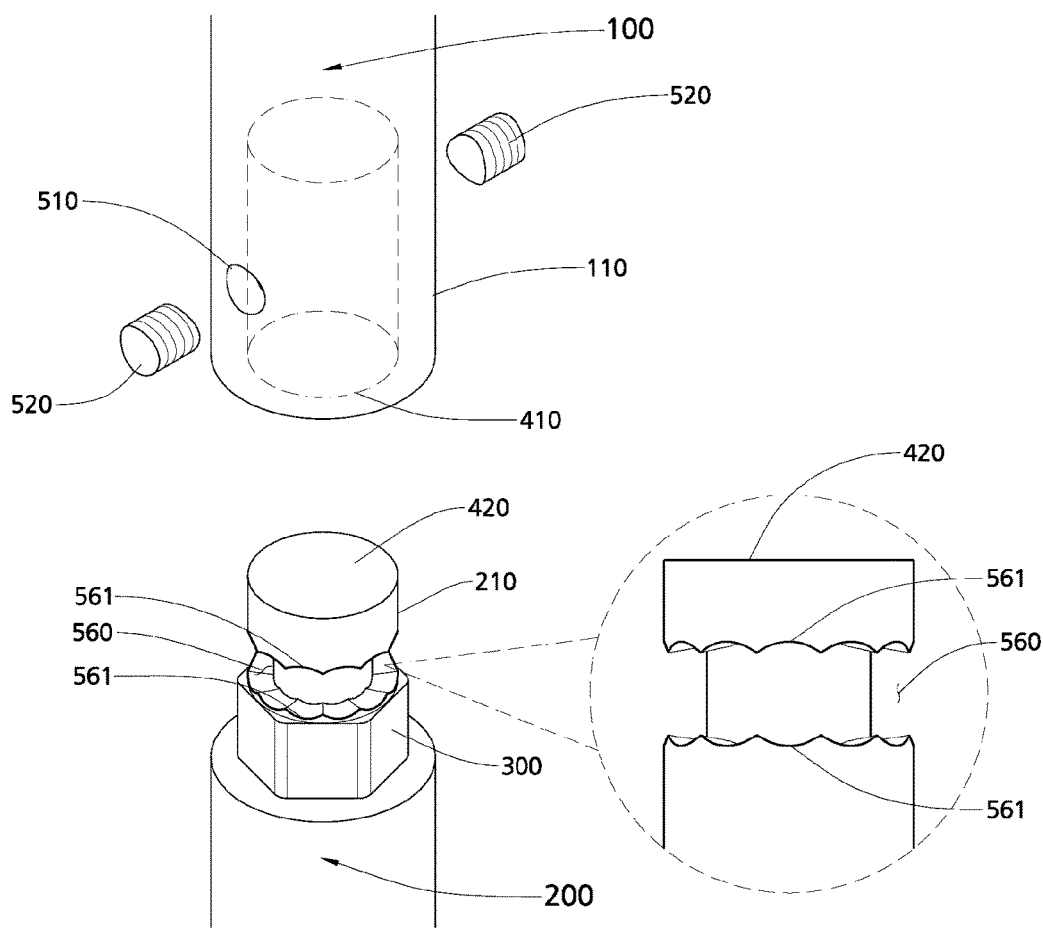

FIG. 13 is a disassembled perspective view illustrating a detachable medical cutting tool in accordance with a fifth embodiment. FIG. 14 is a view illustrating a combination portion of the detachable medical cutting tool of FIG. 13 in accordance with example embodiment.

The detachable medical cutting tool is substantially the same as or similar to that of FIGS. 2 to 5 except for a combination part instead of a coherence keeping portion in a combination between a connection portion of a shank portion and a combination portion of a cutting edge portion. Thus, the same or like reference numerals will be used to refer to the same or like elements and any further repetitive explanation concerning the above elements will be omitted.

As illustrated in FIG. 13, a detachable medical cutting tool in accordance with a fifth embodiment may include a shank portion 100, a cutting edge portion 200, a rotation prevention portion 300 and a combination part 400. The shank portion 100 may include a connection portion 110. The cutting edge portion 200 may includes a combination portion 210 to be combined removably with the connection portion 110 of the shank portion 100. A drill edge may be provided at an outer surface of the cutting edge portion 200. The rotation prevention portion 300 may be interposed between the connection portion 110 of the shank portion 100 and the combination portion 210 of the cutting edge portion 200. The rotation prevention portion 300 prevents from a rotation in a rotation direction. The combination part may combine the cutting edge portion 200 with the shank portion 100, removably.

The combination part may include a combination groove 410, a combination protrusion 420 and a fixing portion. The combination groove 410 may be arranged in the connection portion 110 of the shank portion 100. The combination protrusion 420 may be arranged at the combination portion 210 of the cutting edge portion 200. The combination protrusion 420 may be inserted in the combination groove 410.

The fixing portion may fix the combination portion 210 to the connection portion 110. The fixing portion may include a combination hole 510, a fix hole 530 and a combination member 520.

The combination hole 510 may have an inner screw thread. The combination hole 510 may penetrate the combination groove 410 in a perpendicular direction to the combination groove 410 from an outer surface of the shank portion 100. The fix hole 530 may penetrate the combination protrusion 420 in a perpendicular direction to the combination protrusion 420 at an end of the cutting edge portion 200. The combination member 520 may be fixed to the fix hole 530 near the cutting edge portion 200 through the combination hole 510 near the shank portion 100.

A plurality of fix holes 530 with which the combination member 520 is combined may be arranged in a circumferential direction at the combination protrusion 420 near the cutting edge portion 200. Accordingly, when the combination member 520 is combined with one of the fix holes 530 though the combination hole 510 near the connection portion 110, the combination member 530 may be easily combined with one of the fix holes 530.

The combination member 520 may include a bolt, preferably, a striper bolt.

The detachable medical cutting tools may further include a position marker 550. The position marker 550 may be arranged at an outer surface of the cutting edge portion 200 in a virtual extension line crossing a center of each of the fix holes 530 to represent a position of each of the fix holes 530.

By the position marker 530, the position of each of the fix holes 530 may be easily known and the combination member 530 may be easily combined with one of the fix holes 530 when the combination protrusion 420 is inserted in the combination groove 410 and the fix holes 530 are hidden.

Referring to FIG. 14, the combination protrusion 420 may include an annular groove 560. A respective one of combination surfaces 561 having a round waveform corresponding to an outer surface of the stripper bolt may be formed at a respective one of top and bottom surfaces of the annular groove 560.

Figure 15:
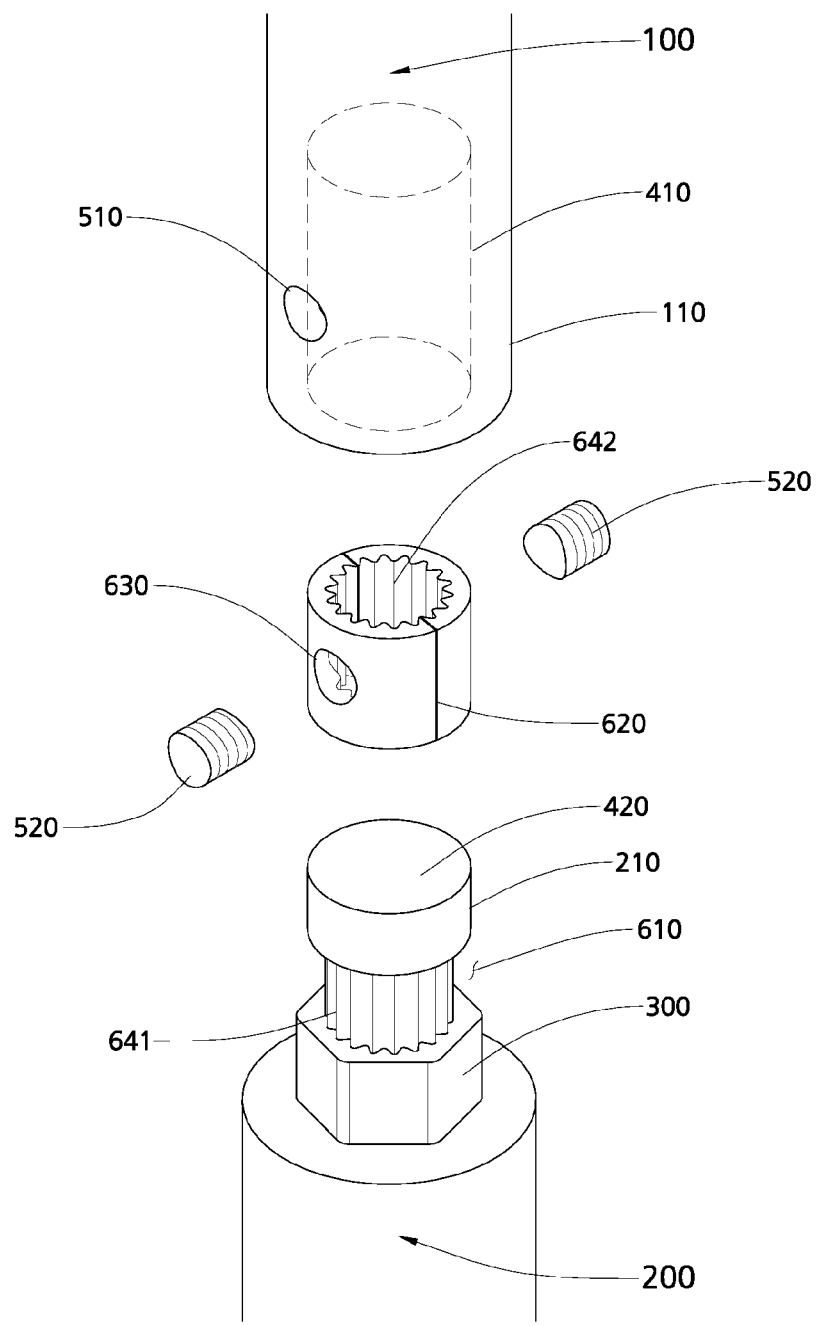

FIG. 15 is a disassembled perspective view partially illustrating a detachable medical cutting tool in accordance with a sixth embodiment.

The detachable medical cutting tool is substantially the same as or similar to that of FIGS. 13 and 14 except for a combination part in a combination between a connection portion of a shank portion and a combination portion of a cutting edge portion. Thus, the same or like reference numerals will be used to refer to the same or like elements and any further repetitive explanation concerning the above elements will be omitted.

As illustrated in FIG. 15, a detachable medical cutting tool in accordance with a fifth embodiment may include a shank portion 100, a cutting edge portion 200, a rotation prevention portion 300 and a combination part 400. The shank portion 100 may include a connection portion 110. The cutting edge portion 200 may includes a combination portion 210 to be combined removably with the connection portion 110 of the shank portion 100. A drill edge may be provided at an outer surface of the cutting edge portion 200. The rotation prevention portion 300 may be interposed between the connection portion 110 of the shank portion 100 and the combination portion 210 of the cutting edge portion 200. The rotation prevention portion 300 prevents from a rotation in a rotation direction. The combination part may combine the cutting edge portion 200 with the shank portion 100, removably.

The combination part may include a combination groove 410, a combination protrusion 420 and a fixing portion. The combination groove 410 may be arranged in the connection portion 110 of the shank portion 100. The combination protrusion 420 may be arranged at the combination portion 210 of the cutting edge portion 200. The combination protrusion 420 may be inserted in the combination groove 410.

The fixing portion may fix the combination portion 210 to the connection portion 110. The fixing portion may include a combination hole 510, a combination carrier portion and a combination member 520.

The combination hole 510 may have an inner screw thread. The combination hole 510 may penetrate the combination groove 410 in a perpendicular direction to the combination groove 410 from an outer surface of the shank portion 100. The combination carrier portion may be interposed between the combination groove 410 and the combination protrusion 420 to increase a combination area. The combination member 520 may be fixed to the combination carrier portion near the cutting edge portion 200 through the combination hole 510 near the shank portion 100.

The combination carrier portion may include an annular groove 610, a ring member 620, a penetration hole 630 and a friction growth portion. The annular groove 610 may be arranged at the combination protrusion 420. The ring member 620 may be installed at the annular groove 610. The penetration hole 630 may be arranged at the ring member 620, and the penetrating hole 630 may have an inner screw thread. The friction growth portion may be interposed between the annular groove 610 and the ring member 620.

As illustrated in FIG. 15, the friction growth portion may include a first jagged portion 641 and a second jagged portion 642. The first jagged portion 641 may be arranged at an outer surface of the annular groove 610. The first jagged portion may have a sawtooth shape. The second jagged portion 642 may be arranged in an inner surface of the ring member 620. The second jagged portion may correspond to the first jagged portion.

According to example embodiments, a detachable medical cutting tool may include a shank portion and a cutting portion including a dual structure of material and composition such that material of main body is reduced, economic feasibility is enhanced, easy detachability is obtained, strong coherence is obtained in a combination mode, durability and a cutting force increase, friction heat decreases, and tissue damage by friction heat of a cutting edge portion is prevented.

The cutting edge portion 200 including the zirconia, stabilized zirconia or alumina may be manufactured by a powder compression sintering method or a manufacturing method of an artificial sapphire such as a skull mult method such that the cutting edge portion 200 has a high density, a friction coefficient lower than a friction coefficient of the stainless steel, chemical resistance, corrosion resistance and bioaffinity.

The cutting edge portion 200 having the zirconia has a high density and a low friction coefficient such that a friction heat of the cutting edge portion 200 by a perforation procedure at high speed rotation is lower than a friction heat of a cutting edge portion including the stainless steel. Additionally, cooling process of spraying a coolant such as saline solution is not necessary and a side effect such as an allergy to a metal material in the perforation procedure at a bone tissue does not occur. In particular, for example, the friction heat cannot be transferred into a neuron of the alveolar bone and a necrosis of the neuron does not occur. A delicate and detailed perforation procedure can be performed such that a good osseointegration after the implant procedure can be expected.

The shank portion 100 including the stainless steel may be not brittle and the shank portion 100 can be used during a long period when the shank portion 100 is attached or detached to the handpiece, repeatedly.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present inventive concept. Accordingly, all such modifications are intended to be included within the scope of the present inventive concept as defined in the claims. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A detachable medical cutting tool configured to be combined with a high speed rotation apparatus comprising:
   a stainless steel shank portion including a connection portion;
   a zirconia cutting edge portion including a combination portion, wherein the combination portion combines with the connection portion of the shank portion;
   a rotation prevention portion disposed on the cutting edge portion and interposed between the connection portion of the shank portion and the combination portion of the cutting edge portion, the rotation prevention portion prevents a rotation of the shank portion and the cutting edge portion against each other; and
   a coupling portion to couple the connection portion of the shank portion and the combination portion of the cutting edge portion with each other, the coupling portion further including at least one of a coupling member or a fixing portion,
   wherein the coupling member includes:
      a combination groove arranged in one of the connection portion of the shank portion and the combination portion of the cutting edge portion, and
      a combination protrusion arranged at the other of the connection portion of the shank portion and the combination portion of the cutting edge portion, the combination protrusion inserted in the combination groove; and
   wherein the fixing member includes:
      a combination hole having an inner screw thread, the combination hole penetrating the combination groove in a perpendicular direction to the combination groove,
      a fix hole penetrating the combination protrusion in a perpendicular direction to the combination protrusion, and
      a combination member fixed to the fix hole through the combination hole.

2. The detachable medical cutting tool of claim 1, wherein the coupling member includes one of a C-ring, an O-ring and a cut annular ring, and
   wherein a portion of the cut annular ring is removed, and ends of the cut annular ring are crossed.

3. The detachable medical cutting tool of claim 2, wherein an outer diameter of the C-ring and the cut annular ring is substantially greater than an inner diameter of the combination groove.

4. The detachable medical cutting tool of claim 1, wherein the combination protrusion is narrowed and tapered toward an end,
   wherein the combination groove is tapered corresponding to the combination protrusion, and
   wherein the installation groove is arranged in an inner surface of the combination groove.

5. The detachable medical cutting tool of claim 4, wherein the coupling member includes one of a C-ring, an O-ring and a cut annular ring,
   wherein a portion of the cut annular ring is removed, and ends of the cut annular ring are crossed, and
   wherein the C-ring, the O-ring or the cut annular ring has a round stepped cross-sectional shape with two stages.

6. The detachable medical cutting tool of claim 5, wherein the C-ring, the O-ring and the cut annular ring are made from an elastic material.

7. The detachable medical cutting tool of claim 1, wherein the coupling portion includes a leaf spring having an annular shape.

8. The detachable medical cutting tool of claim 2, wherein a first jagged portion having a sawtooth shape is arranged at an inner surface of the C-ring or the cut annular ring when the C-ring or the cut annular ring is installed on the combination protrusion, and
   wherein a second jagged portion having a sawtooth shape is arranged at an installation surface of the combination protrusion on which the C-ring or the cut annular ring is installed.

9. The detachable medical cutting tool of claim 1, wherein the one of the connection portion of the shank portion and the combination portion of the cutting edge portion is divided into more than two pieces, and
   wherein the combination groove has a linear shape or a tapered shape in a cross-sectional view.

10. The detachable medical cutting tool of claim 1, further comprising:
    a position marker at an outer surface of the cutting edge portion in a virtual extension line crossing a center of the fix hole to represent a position of the fix hole.

11. The detachable medical cutting tool of claim 1, wherein the combination protrusion includes an annular groove, wherein the combination member includes a stripper bolt, and wherein a combination surface having a round waveform corresponding to an outer surface of the stripper bolt is formed at each of top and bottom surfaces of the annular groove.

12. The detachable medical cutting tool of claim 1, wherein the coupling member includes:
   a combination carrier portion interposed between the combination groove and the combination protrusion to increase a combination area; and
   a combination member combined with the combination carrier portion through the combination hole.

13. The detachable medical cutting tool of claim 12, wherein the combination carrier portion includes:
   an annular groove arranged at the combination protrusion;
   a ring member installed at the annular groove;
   a penetration hole arranged at the ring member; and
   a friction growth portion interposed between the annular groove and the ring member.

14. The detachable medical cutting tool of claim 13, wherein the friction growth portion includes:
   a first jagged portion arranged at an outer surface of the annular groove, the jagged portion having a sawtooth shape; and
   a second jagged portion arranged in an inner surface of the ring member and having a sawtooth shape, the second jagged portion corresponding to the first jagged portion.

15. The detachable medical cutting tool of claim 1, wherein the rotation prevention portion is arranged at each of an end of the connection portion and an end of the combination portion, and
   wherein the rotation prevention portion has one of an elliptical shape, a polygonal shape and a jagged sawtooth shape in a cross-sectional view.

* * * * *